United States Patent [19] [11] 4,357,352
Swallow [45] Nov. 2, 1982

[54] ANTIVIRAL TETRACYCLONONANE DERIVATIVES, PROCESSES FOR THEIR MANUFACTURE AND PHARMACEUTICAL COMPOSITIONS CONTAINING THEM

[75] Inventor: Douglas L. Swallow, Macclesfield, England

[73] Assignee: Imperial Chemical Industries Limited, London, England

[21] Appl. No.: 967,794

[22] Filed: Dec. 4, 1978

[30] Foreign Application Priority Data

Dec. 22, 1977 [GB] United Kingdom ............. 53446/77

[51] Int. Cl.³ ............................................. A01N 33/02
[52] U.S. Cl. ................................. 424/330; 260/501.1; 260/501.21; 424/316; 564/336; 564/453; 564/455; 564/456
[58] Field of Search ............. 260/563 P, 570.5, 501.1, 260/501.21; 424/330, 316; 564/336, 453, 455, 456

[56] References Cited

U.S. PATENT DOCUMENTS 3,418,368 12/1968 Dunn et al. ........................ 260/563
3,456,008 7/1969 Stedman .............................. 260/563
3,496,228 2/1970 Hoover ............................... 260/563

FOREIGN PATENT DOCUMENTS 1180749 2/1970 United Kingdom .

OTHER PUBLICATIONS

Hall, "Journal Organic Chemistry", vol. 25, pp. 42-44 (1960).

Primary Examiner—Robert V. Hines
Attorney, Agent, or Firm—Cushman, Darby & Cushman

[57] ABSTRACT

The invention relates to a pharmaceutical composition comprising a tetracyclononane derivative of the formula:

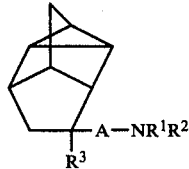

wherein $R^1$, $R^2$ and $R^3$ are hydrogen atoms or alkyl radicals and A is $CH_2CH_2$ or $CH—R^4$ in which $R^4$ is a hydrogen atom or an alkyl, cyclohexyl, phenylalkyl or optionally-substituted phenyl radical, or a salt thereof. The majority of compounds of the formula II are novel and they are included within the scope of the invention, as are processes for their manufacture. Typical of the compounds disclosed is 8-(1-amino-ethyl)tetracyclo-[4,3,0,0²,⁴,0³,⁷]nonane.

4 Claims, No Drawings

ANTIVIRAL TETRACYCLONONANE DERIVATIVES, PROCESSES FOR THEIR MANUFACTURE AND PHARMACEUTICAL COMPOSITIONS CONTAINING THEM

This invention relates to amino derivatives of tetracyclo[4,3,0,0$^{2,4}$,0$^{3,7}$]nonane which possess antiviral properties.

It is claimed that 8-aminotetracyclo[4,3,0,0$^{2,4}$,0$^{3,7}$]nonane has antiviral properties (U.K. Pat. No. 1,180,749). It is also known that 1-aminoadamantane has activity against influenza virus A$_2$. (W. L. Davies et al., *Science*, 1964, 144, 862). It has now been discovered that the known compound 8-aminomethyl-tetracyclo[4,3,0,0$^{2,4}$,0$^{3,7}$]nonane (H. K. Hall, *J. Org. Chem.*, 1960, 25, 42) and a number of novel substituted derivatives thereof have high activity, both in vitro and in vivo, against a range of influenza viruses.

The tetracyclo[4,3,0,0$^{2,4}$0,$^{3,7}$]nonane ring system is numbered as follows:

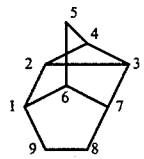

I

A substituent at the 8-position which lies above the plane formed by carbon atoms 1,6,7,8 and 9 is defined as having the exo-configuration. A substituent at the 8-position which lies below this plane is defined as having the endo- configuration.

According to the invention there is provided a pharmaceutical composition comprising a tetracyclononane derivative of the formula:

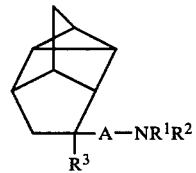

II wherein R$^1$, R$^2$ and R$^3$, which may be the same or different, are hydrogen atoms or alkyl radicals of 1 to 3 carbon atoms and A is a radical of the formula CH$_2$CH$_2$ or CH-R$^4$ in which R$^4$ is a hydrogen atom or an alkyl radical of 1 to 6 carbon atoms, a cyclohexyl radical, a phenylalkyl radical in which the alkyl part is of 1 to 6 carbon atoms, or a phenyl radical optionally substituted by a halogen atom or by an alkyl or alkoxy radical of 1 to 6 carbon atoms; or a pharmaceutically-acceptable acid-addition salt thereof, together with a pharmaceutically-acceptable diluent or carrier.

It will be observed that the compound of the formula II may exist in several isomeric forms due to the relative geometric placing of the substituents A, R$^3$ and R$^4$. It is to be understood that this invention encompasses each of these isomers, whether singly or in admixture.

It will also be observed that the exo or endo isomer of the formula II possesses one or two asymmetric centres, namely the carbon atoms carrying R$^3$ and R$^4$. Where two asymmetric centres are present, each exo and endo isomer can of course occur in two diastereoisomeric forms. The racemic form of any individual isomer of the formula II may therefore be resolved into two optically-active enantiomers. It is to be understood that this invention encompasses the racemic form of the individual isomer of the formula II, and in addition any optical isomer which possesses the useful properties of the composition of the invention, as hereafter defined, it being a matter of common general knowledge to those skilled in the art how such isomers, both geometric and optical, may be separated, and how their biological properties may be determined.

The composition of the invention may be obtained by conventional means using conventional diluents or carriers, and may be in a form suitable for oral administration, for example in the form of a tablet, aqueous or oily solution or suspension, emulsion, dispersible powder, granules, syrup or elixir; or for parenteral administration, for example in the form of a sterile injectible aqueous or oily solution or suspension; or for nasal administration, for example in the form of a snuff or nasal drops, spray or aerosol; or for rectal administration, for example in the form of a suppository.

Examples of particular formulations are described in Examples 1 to 3. It will be recognised by those skilled in this art that these formulations represent only particular methods of preparing such formulations, and, for example, the strength of the dosage form may be varied to satisfy particular requirements.

All the compounds of the formula II apart from that in which A is CHR$^4$ and R$^1$, R$^2$, R$^3$ and R$^4$ are all hydrogen atoms, are novel, and these novel compounds are therefore provided as a further feature of the invention.

Therefore, according to a further feature of the invention, there is provided a tetracyclononane derivative of the formula II in which R$^1$, R$^2$, and R$^3$, which may be the same or different, are hydrogen atoms or alkyl radicals of 1 to 3 carbon atoms and A is a radical of the formula CH$_2$CH$_2$ or CH—R$^4$ in which R$^4$ is a hydrogen atom or an alkyl radical of 1 to 6 carbon atoms, a cyclohexyl radical, a phenylalkyl radical in which the alkyl part is of 1 to 6 carbon atoms, or a phenyl radical optionally substituted by a halogen atom or by an alkyl or alkoxy radical of 1 to 6 carbon atoms, provided that when A is a radical of the formula CHR$^4$ at least one of R$^1$, R$^2$, R$^3$ and R$^4$ is other than a hydrogen atom; and the pharmaceutically acceptable acid-addition salts thereof.

A particular value for R$^1$, R$^2$ or R$^3$ when it is an alkyl radical is a methyl radical.

A particular value for R$^4$ when it is an alkyl radical is a methyl, ethyl, n-propyl or i-propyl radical.

A particular value for R$^4$ when it is a phenylalkyl radical is a 3-phenylpropyl radical.

A particular value for the optional substituent on R$^4$ when R$^4$ is a phenyl radical is a fluorine, chlorine or bromine atom or a methyl or methoxy radical. A preferred position for such an optional substituent is the 4-position on the phenyl radical.

A suitable pharmaceutically-acceptable acid-addition salt of the compound of the formula II is, for example, a salt formed with an inorganic acid, for example with hydrochloric, hydrobromic, sulphuric or phosphoric acid, a salt formed with a carboxylic acid, for example with acetic, benzoic mandelic, tartaric, adipic, lactic, citric, gluconic, oxalic or succinic acid, or a salt formed with a sulphonic acid, for example methanesulphonic acid or toluene-p-sulphonic acid.

A preferred group of compounds of the invention is that of the formula II in which $R^1$ and $R^2$ are hydrogen atoms, $R^3$ is a hydrogen atom or a methyl radical and A is a radical of the formula $CH_2CH_2$ or $CHR^4$ in which $R^4$ is a methyl radical or a phenyl radical.

A particularly preferred group of compounds of the invention is that of the formula II in which $R^1$, $R^2$ and $R^3$ are hydrogen atoms and A is a radical of the formula $CHR^4$ in which $R^4$ is a methyl radical.

The two particularly preferred compounds of the invention are those of the formula II in which $R^1$, $R^2$ and $R^3$ are hydrogen atoms and A, which is in the exo configuration, is a radical of the formula $CHR^4$ in which $R^4$ is a methyl radical, that is the two diastereoisomers described by name exo-8-(1-aminoethyl)tetracyclo[4,3,0,0,$^{2,4}$,0$^{3,7}$]nonane.

The tetracyclononane derivative of the invention may be manufactured by methods known in themselves for the manufacture of chemically-analogous compounds. The following processes, A, $R^1$, $R^2$, $R^3$ and $R^4$ having the meanings stated above, are therefore provided as further features of the invention. The process of the invention is characterised by:

(a) for those compounds in which $R^1$ and $R^2$ are hydrogen atoms, reduction of a compound of the formula:

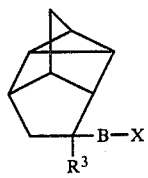

III in which B is a methylene radical or a direct bond and X is a cyano or carbamoyl radical or a radical of the formula:

IV in which $R^5$ is a hydrogen atom or hydroxy radical or a radical of the formula Mg-Y in which Y is a chlorine, bromine or iodine atom, provided that when B is a methylene radical, $R^4$ is a hydrogen atom, and provided that, when B is a direct bond at least one of $R^3$ and $R^4$ is other than a hydrogen atom;

(b) for those compounds in which at least one of $R^1$ and $R^2$ is an alkyl radical, alkylation of the corresponding NH compound by conventional means;

(c) for those compounds in which at least one of $R^1$ and $R^2$ is a hydrogen atom, hydrolysis of the corresponding compound in which the nitrogen atom carries an acyl radical; or (d) for a compound which is an optically active enantiomer, resolution of the racemic compound of the formula II or use of either of processes (b) or (c) in which the starting material is itself a resolved isomer.

When the compound of the formula II is obtained in the form of the free base and a salt is required, the base is reacted with an acid which affords a pharmaceutically-acceptable anion.

Process (a) may be carried out using a complex hydride reducing agent, for example lithium aluminium hydride, in a diluent or solvent such as ether. The reaction may be accelerated or completed by the application of heat. Alternatively process (a) may be carried out by hydrogenation in the presence of a catalyst such as rhodium on alumina and in a diluent or solvent such as ethanol. The reaction may be accelerated or completed by carrying out the hydrogenation at high pressure, for example at 50 atmospheres and/or at high temperature, for example at 60°–65° C.

Process (b) may be carried out by alkylation of the NH compound with an alkylating agent such as a dialkyl sulphate, for example dimethyl sulphate, or an alkyl halide, for example methyl iodide. Alternatively the NH compound may be acylated and the N-acyl derivative reduced with a reducing agent such as lithium aluminium hydride or sodium cyanoborohydride.

Process (c) may be carried out using aqueous or aqueous alcoholic sodium or potassium hydroxide.

The starting material of the formula III in which $R^4$ is other than a hydrogen atom and $R^5$ is Mg-Y may be prepared by reaction of the appropriate 8-cyano compound with a Grignard reagent, for example as described in Examples 4 and 5.

The starting material of the formula III in which $R^5$ is a hydroxy radical may be prepared by reaction of the corresponding carbonyl compound with hydroxylamine, for example as described in Example 6. The carbonyl intermediate in which $R^4$ is other than a hydrogen atom may be prepared by a Grignard reaction on the corresponding 8-cyano compound, for example as described in Example 6.

The intermediate leading to starting material of the formula III in which $R^3$ is an alkyl radical may be prepared by alkylation of the corresponding 8-cyano compound, for example as described in Example 9.

The starting material of the formula III in which B is a methylene radical, $R^3$ is a hydrogen atom and X is a cyano radical may be prepared as described in Example 11.

The starting material for use in process (c) may be prepared by acylation in pyridine of the corresponding oxime followed by reduction of the double bond and hydrolysis of the acyl product, for example as described in Example 14.

As stated above, the compositions and compounds of the invention possess activity against a range of influenza viruses. This activity may be demonstrated in an in vitro test against virus grown in calf kidney cells, but is better demonstrated in a test against virus grown in ferret tracheal rings. This latter test is a much more reliable indicator of activity since it employs segments of target organ from a warm blooded animal and is therefore intermediate between a pure in vitro and a pure in vivo test. Further, the preferred compounds and compositions of the invention, when tested in mice, show good ability to reduce influenza virus growth in the lungs of infected animals.

The test on ferret tracheal rings is carried out as follows:

The trachea of a 3-month old ferret is dissected out using aseptic techniques and cut transversely into rings of tissue. About 30–40 rings per trachea are obtained. Each ring is placed in a sterile glass test tube (9×1 cm.) and covered with 0.5 ml. sterile maintenance medium containing an appropriate concentrations of test compound. Final compound concentrations are 45 µg/ml, 9 µg/ml, 1.8 µg/ml, 0.4 µg/ml, 0.08 µg/ml and zero. Three tubes are used for each concentration. The tubes are incubated overnight at 37° C. in a rack which is gently rolled to bathe each tracheal ring in the nutrient medium.

The next morning each ring is examined under a low power microscope to determine what approximate proportion of cilia on the internal lumen of the ring is still beating. Scoring is:

| | |
|---|---|
| 4 = | 100% of cilia still beating |
| 3 = | 75% of cilia still beating |
| 2 = | 50% of cilia still beating |
| 1 = | 25% of cilia still beating |
| 0 = | 0% of cilia still beating |

This initial examination shows whether the compound alone is toxic to ciliated epithelium. Each tube is then infected by adding a standardised amount of influenza virus and left to incubate for 2 hours at 37° C. During this time the virus is adsorbed onto and into the cells of each ring and the infectious process begins. After 2 hours, the virus containing liquors are decanted off, the rings washed gently with fresh medium and then a further 0.5 ml. of compound-containing medium added. They are then incubated at 37° C. as before until the next morning, when a second examination of the ciliated epithelium takes place. Scoring of uninfected control shows the extent of drug toxicity, of infected but no drug control the extent of virus-mediated damage, and of the drug treated the extent of protection. The medium is removed from each tube and pooled with that from the other 2 tubes of identical drug concentration. The pooled samples are treated with 0.3 ml. sterile bovine plasma albumin, frozen at −20° C. and stored for future titration of virus. Fresh drug solution is added to each set of 3 tubes and incubation continued. The above process is repeated 3 more times so that, in all, 4 lots of media are obtained from each drug dilution and the controls. The frozen media samples are thawed to 37° C. and the virus which they contain is titrated in primary calf kidney cells using the published quantitative haemadsorption method (N. B. Finter, *Ann. N.Y. Acad. Sci.*, 1970, 173, 131). It is thus possible to compare both visually and quantitively the effect of a test compound on the growth of influenza virus in pieces of tracheal ciliated epithelium.

All the compounds exemplified in this specification are active on this test against Influenza $A_1$ and $A_2$ viruses and some compounds are also active against Influenza $A_0$ virus. Thus all the compounds exemplified in this specification are active on this test against Influenza $A_2HK$ virus at or below a concentration of 5 μg./ml. and have a toxicity/activity ratio ranging from 9 to greater than 550. The known compound 8-aminotetracyclo[4,3,0,0$^{2,4}$,0$^{3,7}$]nonane is not active at a concentration of 50 μg/ml. against Influenza $A_2HK$ virus on this test.

The test against influenza virus in mice is carried out as follows:

Two groups of 10 specific pathogen free white male mice weighing 20–22 g. each are dosed orally with the test compound, one group at 125 mg./kg. (2.5 mg./mouse) and one group at 50 mg./kg. (1.0 mg./mouse). A third group of 10 is not treated with compound and is used as a control group. Two hours later the mice are placed individually in an aerosol chamber and exposed for 0.5 hours to an aerosol of influenza virus. One hour after infection and again 4 hours after infection the mice in the first 2 groups are dosed orally with test compound. Next day the same mice are dosed with test compound at 9.0 am., 1.0 p.m. and 5.0 p.m. 48 Hours after infection all the mice are killed and the lungs excised. Lungs from each separate group are pooled in 2 groups of 5, and after examination for lesions on the surface of the lungs, each of the 6 groups is homogenised in a blender with Hanks sterile saline. The homogenates are centrifuged to remove tissue debris and the supernatant bottled and diluted with 9 parts of bovine plasma albumin. The diluted supernatants are then stored at −20° C. until the virus concentration in each can be assayed by the quantitative haemadsorption method described above. Thus the virus growth in the lungs of drug treated mice can be compared with the virus growth in untreated mice and a measure of the efficacy of the drug obtained.

Mice receiving test compound show no overt signs of toxicity attributable to the compound on this test.

In treating an influenza infection using a composition of the invention, it is preferable to use one which will enable the tetracyclononane derivative of the invention to produce a virucidal level in the parts of the body where influenza viruses normally grow, for example the mucosae of the nose, mouth, throat and bronchi, either by direct application of the composition to those parts, or indirectly by producing a sufficient blood level of the antiviral compound after dosing.

Such preferred compositions for direct application are, for example, lozenges which may be dissolved slowly in the mouth, in order to bathe the mouth and associated passages with a solution or suspension of the active ingredient, and nasal sprays or wet aerosols in the form of a solution or suspension of the tetracyclononane derivative in an inert pharmaceutically-acceptable liquid, or a dry powder aerosol which contains the tetracyclononane derivative in finely powdered form, any of which may be inhaled and deposited in the nasal and bronchial passages, and preferred compositions for oral dosage are, for example, tablets giving a sufficient blood level.

A suitable tablet or lozenge for human use contains between 10 and 500 mg. of the antiviral compound, or between 10 and 200 mg. of a preferred compound of the invention. A regimen for prophylaxis or treatment of influenza in man is one to three tablets 2 to 4 times per day.

A suitable nasal spray or aerosol for human use contains from 2 mg. to 300 mg. of the tetracyclononane derivative per ml. of solution or suspension or 2 mg. to 40 mg. per ml. of a preferred compound of the invention, and for prophylaxis or treatment of influenza in man about 0.25–1 ml. of such solution or suspension is dropped or sprayed into the nose of the subject 3 to 6 times per day.

The composition of the invention may also contain other known useful compounds, for example antiviral agents such as amantadine, nasal decongestants, antipyretics or antiseptics.

The invention is illustrated, but not limited, by the following Examples:

EXAMPLE 1

A mixture of sucrose (88 g.), magnesium (1 g.), gum acacia (3 g.), water (3 ml.) and 8-aminomethyltetracyclo[4,3,0,0$^{2,4}$,0$^{3,7}$]nonane hydrochloride (5 g.) was blended and then compressed into hard lozenges, such that each lozenge weighed 1.0 g. Such a lozenge contained 50 mg. of 8-aminomethyltetrcyclo[4,3,0,0$^{2,4}$,0$^{3,7}$]nonane hydrochloride.

EXAMPLE 2

A solution of 8-aminomethyltetracyclo[4,3,0,0$^{2,4}$,0$^{3,7}$-]nonane hydrochloride (1.0 g.) in sterile distilled water (99 g.) containing chlorbutol (0.5% w/w), was filled into squeezable plastic containers which were each closed with a nozzle suitable for producing a coarse spray when the container was squeezed. There was thus obtained a spray composition suitable for administration by inhalation.

EXAMPLE 3

An intimate mixture of 8-aminomethyltetracyclo[4,3,0,0$^{2,4}$,0$^{3,7}$]nonane hydrochloride (33 g.), maize starch (22.5 g.), calcium phosphate (44.0 g.) and magnesium stearate (0.5 g.) was compressed, and the compressed mixture was then broken down into granules by passage through a 16-mesh screen. The resultant granules were compressed into tablets, each of which contained 50 mg. of active ingredient.

EXAMPLE 4

A solution of methyl magnesium iodide was prepared from magnesium (12.0 g.) and methyl iodide (71.0 g.) in ether (400 ml.). The ether was distilled off and replaced simultaneously with dry toluene (300 ml.). To the toluene solution was added 8-cyanotetracyclo[4,3,0,0$^{2,4}$,0$^{3,7}$-]nonane (58.0 g.) (prepared as described by Schrauzer and Glockner, Chem.Ber.,1964, 97, 2451 and shown by gas liquid chromatography to be a mixture of exo and endo in the ratio 3.6:1) and the mixture heated under reflux until all the nitrile had reacted (about 6 hours). This solution was cooled to ambient temperature and a suspension of lithium aluminium hydride (7.6 g.) in anhydrous ether (200 ml.) added slowly with stirring. The mixture was heated under reflux for 6 hours, cooled to ambient temperature and excess lithium aluminium hydride destroyed by carefully adding water dropwise with vigorous stirring. Dilute caustic soda solution (15 ml. 18.6 N NaOH in 50 ml. water) was then added to decompose the Grignard complex. The precipitated solids were filtered from the liquors and washed thoroughly with ether. The combined liquors and washings were dried over anhydrous potassium carbonate, filtered and treated with an excess of dry hydrogen chloride gas. There was thus obtained a precipitate of 8-(1-aminoethyl)tetracyclo[4,3,0,0$^{2,4}$,0$^{3,7}$]nonane hydrochloride which was filtered off, washed with ether, dried and recrystallised from isopropyl alcohol. This product had a melting point of 265.5°–266° C.

EXAMPLE 5

In a similar manner to Example 4, but using the appropriate alkyl, arylalkyl or aryl halide in place of methyl iodide, the following analogues were prepared:

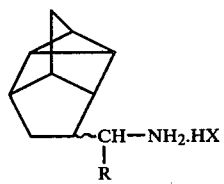

| Halide | R | X | m.p. °C. |
|---|---|---|---|
| Ethyl iodide | —CH$_2$CH$_3$ | Cl | 229–231 |
| n-Propyl bromide | —CH$_2$CH$_2$CH$_3$ | benzoate | 185–187 |
| i-Propyl bromide | —CH(CH$_3$)$_2$ | benzoate | 176–178 |
| Cyclohexyl bromide | —C$_6$H$_{11}$ | benzoate | 114–116 |
| Phenylpropyl bromide | —(CH$_2$)$_3$—C$_6$H$_5$ | Cl | 148–150 |
| Bromobenzene | —C$_6$H$_5$ | benzoate | 158–160 |
| p-Chlorobromobenzene | —C$_6$H$_4$—Cl | benzoate | 198–201 |
| p-Bromoanisole | —C$_6$H$_4$—OCH$_3$ | benzoate | 188–191 |
| p-Bromotoluene | —C$_6$H$_4$—CH$_3$ | benzoate | 217–219 |

EXAMPLE 6

Exo-8-(1-oximinoethyl)tetracyclo[4,3,0,0$^{2,4}$,0$^{3,7}$]nonane (3.0 g.) was dissolved in dry ether (20 ml.) at ambient temperature and added dropwise with stirring to a refluxing suspension of lithium aluminium hydride (1.0 g.) in dry ether (50 ml.). When additon was complete the mixture was heated under reflux for a further 16 hours, cooled and water added carefully dropwise to decompose excess lithium aluminium hydride. The solids were filtered off from the organic phase and washed thoroughly with ether. The organic phase and washings were combined, dried over anhydrous K$_2$CO$_3$, filtered and treated with an excess of dry hydrogen chloride in ether. A white precipitate of exo-8-(1-aminoethyl)tetracyclo[4,3,0,0$^{2,4}$,0$^{3,7}$]nonane hydrochloride was thus obtained which was recrystallised from isopropyl alcohol. The recrystallised product had m.p. 254°–255° C.

The exo-8-(1-oximinoethyl)tetracyclo[4,3,0,0$^{2,4}$,0$^{3,7}$-]nonane used as starting material may be prepared in the following manner:

8-Cyanotetracyclo[4,3,0,0$^{2,4}$,0$^{3,7}$]nonane (29 g.) was treated with methyl magnesium iodide from magnesium (6.0 g.) and methyl iodide (35.5 g.) as in Example 4 to give a solution of the Grignard complex of the nitrile in toluene. This solution was cooled to below 5° C. in an ice bath and a cold solution of glacial acetic acid (25 ml.) in water (25 ml.) added dropwise with stirring and cooling. The temperature was not allowed to rise above 15° C. To the thick suspension was added water (150 ml.) and stirring continued until the solids dissolved. The organic phase was separated, washed three times with water (50 ml.), dried over anhydrous magnesium sulphate and filtered. The toluene was evaporated off on a rotary evaporator and the residual oil distilled under high vacuum. There was thus obtained a mixture of exo- and endo-8-acetyltetracyclo[4,3,0,0$^{2,4}$,0$^{3,7}$]nonane, b.p. 66° C./0.5 mm.

The above acetyl derivative (16.2 g.) was dissolved in ethanol (60 ml.) and to the solution was added hydroxylamine hydrochloride (7.6 g.) and anhydrous sodium acetate (12.3 g.). The mixture was heated to reflux and water added in small portions until the solids dissolved completely. Heating under reflux was continued for 21 hours, and the solution was then cooled in an ice bath. A white solid crystallised out and was filtered off. Recrystallisation from a 70:30 mixture of ethanol and water gave exo-8-(1-oximinoethyl)tetracyclo[4,3,0,0$^{2,4}$,0$^{3,7}$]nonane, m.p. 104°-104° C.

EXAMPLE 7

8-cyanotetracyclo[4,3,0,0$^{2,4}$,0$^{3,7}$]nonane was prepared by the method of Hall, *J.Org.Chem.* 1960, 25, 42, and was found to be a 50:50 mixture of exo and endo isomers by gas liquid chromatography.

The isomers were separated by preparative gas liquid chromatography and a pure sample of the exo-isomer was obtained. However, the endo-isomer could only be obtained 80% pure. Separate reduction of these with LiAlH$_4$ in ether gave pure exo-8-aminomethyltetracyclo[4,3,0,0$^{2,4}$,0$^{3,7}$]nonane, m.p. of hydrochloride 270°-271° C., and 80% pure endo-isomer, m.p. of hydrochloride 274°-276° C.

EXAMPLE 8

Exo-8-cyano-endo-8-methyltetracyclo[4,3,0,0$^{2,4}$,0$^{3,7}$]nonane (2.0 g.) was added slowly to a suspension of lithium aluminium hydride (0.6 g.) in diethyl ether (25 ml.). The mixture was heated under reflux for 16 hours. Excess reducing agent was destroyed by careful addition of water. The white precipitate was filtered off, washed well with ether and the washings and filtrate combined, dried over anhydrous K$_2$CO$_3$ and treated with excess hydrogen chloride dissolved in ether. There was obtained exo-8-aminomethyl-endo-8-methyltetracyclo[4,3,0,0$^{2,4}$,0$^{3,7}$]nonane hydrochloride, which after recrystallisation from isopropanol/ethylacetate (25:75 v/v) had m.p. 245°-264° C.

The exo-8-cyano-endo-8-methyltetracyclo[4,3,0,0$^{2,4}$,0$^{3,7}$]nonane used as starting material may be prepared by the method of G. N. Schrauzer and P. Glockner (*Chem.Ber.* 1964, 97,2451.). The quoted yields could not be obtained and extensive purification by column chromatography was required to obtain pure material. This was shown by gas liquid chromatography to be 95% exo-nitrile, 5% endo-nitrile.

EXAMPLE 9

Endo-8-cyano-exo-8-methyltetracyclo[4,3,0,0$^{2,4}$,0$^{3,7}$]nonane (80% endo-cyano isomer, 500 mg.) was reduced with lithium aluminium hydride (0.5 g.) and the reaction mixture worked up exactly as in Example 8. There was thus obtained endo-8-aminomethyl-exo-8-methyltetracyclo[4,3,0,0$^{2,4}$,0$^{3,7}$]nonane hydrochloride (80% endo-aminomethyl, 20% exo-aminomethyl), m.p. 222° C.

The endo-nitrile isomer used as starting material may be obtained in the following manner. Butyl lithium (15.4 ml. of a 1.43×10$^{-3}$ M solution in tetrahydrofuran, 0.022 M) was added slowly to a solution of di-isopropylamine (2.22 g., 0.022 M) in dry tetrahydrofuran (10 ml.) under N$_2$ at 5°-10° C. and stirred for 15 minutes. This solution was cooled to −78° C., and to it was added 8-cyanotetracyclo[4,3,0,0$^{2,4}$,0$^{3,7}$]nonane (3.045 g., 0.022 M) dissolved in hexamethylphosphoramide (4.5 g.). The mixture was stirred 1 hour at −78° C. A solution of methyl iodide (3.55 g., 0.025 M) in dry tetrahydrofuran (5 ml.) was added dropwise also at −78° C. and the mixture stirred for 1.5 hours at this temperature and then for 16 hours at ambient room temperature. Water (20 ml.) was added, the tetrahydrofuran evaporated off in vacuo and the residual mixture extracted with chloroform (3×15 ml.) The extract was dried over MgSO$_4$, filtered and the solvent removed in vacuo. The residue was chromatographed on silica gel with toluene as eluant to give endo-8-cyano-exo-8-methyltetracyclo[4,3,0,0$^{2,4}$,0$^{3,7}$]nonane (80% endo-cyano isomer, 20% exo-cyano isomer by gas liquid chromatography), b.p. 118°-120° C./18 mm.

EXAMPLE 10

8-Aminomethyltetracyclo[4,3,0,0$^{2,4}$,0$^{3,7}$]nonane (1.1 g.) was heated under reflux for 16 hours with ethyl formate. The solvent was removed in vacuo and the residue chromatographed on silica gel with ethyl acetate as eluant to give 8-(N-formylaminomethyl)tetracyclo[4,3,0,0$^{2,4}$,0$^{3,7}$]nonane. This product was reduced in ether solution with lithium aluminium hydride as in previous Examples and the resulting amine precipitated as its hydrochloride. There was thus obtained 8-(N-methylaminomethyl)tetracyclo[4,3,0,0$^{2,4}$,0$^{3,7}$]nonane hydrochloride, m.p. 225°-226° C.

EXAMPLE 11

8-Cyanomethyltetracyclo[4,3,0,0$^{2,4}$,0$^{3,7}$]nonane (0.5 g.) was reduced with lithium aluminium hydride (0.5 g.) using the method described in Example 6. There was thus obtained 8-(2-aminoethyl)tetracyclo[4,3,0,0$^{2,4}$,0$^{3,7}$]nonane hydrochloride, m.p. 252°-254° C.

The 8-cyanomethyltetracyclo[4,3,0,0$^{2,4}$,0$^{3,7}$]nonane used as starting material may be obtained as follows:

To a solution of 8-cyanotetracyclo[4,3,0,0$^{2,4}$,0$^{3,7}$]nonane (87 g.) in carbon tetrachloride (600 ml.) was added phosphorus pentachloride (168 g.). The mixture was heated under reflux for 60 hours, cooled and poured into a mixture of crushed ice and water (1 l.). The mixture was stirred for 30 minutes and the organic layer separated. This was washed with a 10% w/v aqueous solution of sodium carbonate (200 ml.), saturated brine (100 ml.) and then dried over anhydrous potassium carbonate. The filtrate was then evaporated in vacuo to remove solvent and then distilled in vacuo to give 8-cyano-8-chlorotetracyclo[4,3,0,0$^{2,4}$,0$^{3,7}$]nonane, b.p. 136°-140° C./20 mm., in 83% yield.

This chloronitrile (13.45 g.) was dissolved in ethanol (60 ml.), cooled to 0° C. in ice and a solution of sodium hydroxide (2.4 g.) in water (20 ml.) added dropwise with stirring and cooling. Hydrogen peroxide (27 ml. of a 29% w/v solution in water) was added dropwise giving a dense white precipitate. This mixture was stirred for 3 hours at 0° C. and then 2 hours at room temperature. The white precipitate was filtered off and retained. The filtrate was evaporated in vacuo to remove ethanol and the aqueous residue extracted with chloroform (100 ml.). The organic phase was dried, filtered and evaporated to give a white solid. This solid and the white precipitate were combined, and recrystallised from ethanol to give 8-chloro-8-carbamoyltetracyclo[4,3,0,0$^{2,4}$,0$^{3,7}$]nonane m.p. 124°-126° C.

This chloroamide (19.75 g.) was heated under reflux under nitrogen in a mixture of potassium hydroxide (16.8 g.) and n-propanol (200 ml.) for 40 minutes. The propanol was evaporated in vacuo and the residue partitioned between ether and water (100 ml. of each). The organic phase was washed with saturated brine (50 ml.), dried over anhydrous $K_2CO_3$, filtered and the solvent evaporated. The residual oil was distilled in vacuo to give 8-oxotetracyclo[4,3,0,0$^{2,4}$,0$^{3,7}$]nonane, b.p. 124°–130° C./29 mm.

Sodium hydride (2.4 g. washed free of oil) was treated with dimethyl sulphoxide (100 ml.) and warmed under nitrogen to 75°–80° C. for 35 minutes. The mixture was cooled to ambient temperature and a solution of diethyl cyanomethylphosphonate (17.7 g.) in dry tetrahydrofuran (100 ml.) added dropwise. The mixture was stirred for 30 minutes. A solution of the above ketone (13.4 g.) in a mixture of dimethyl sulphoxide (100 ml.) and tetrahydrofuran (100 ml.) was then added dropwise and stirred for 16 hours at room temperature. The product was poured into water (1000 ml.) and the mixture extracted with ether (5×100 ml.). The combined extracts were washed with saturated brine, dried over potassium carbonate, filtered and evaporated. Distilled in vacuo gave 8-cyanomethylenetetracyclo[4,3,0,0$^{2,4}$,0$^{3,7}$]nonane, b.p. 138°–140° C./18 mm.

This unsaturated nitrile (6.17 g.) was reduced in an atmosphere of hydrogen at room temperature and pressure in the presence of 5% w/w palladium on charcoal catalyst (1.7 g.) in ethanol solution (200 ml.). When no more hydrogen was absorbed the reaction was filtered and the solvent evaporated to give 8-cyanomethyltetracyclo[4,3,0,0$^{2,4}$,0$^{3,7}$]nonane, identified by mass spectrum, m/e=159, infra-red spectrum and n.m.r spectrum, which was used without further purification.

EXAMPLE 12

To a solution of endo-8-(1-oximinoethyl)tetracyclo[4,3,0,0$^{2,4}$,0$^{3,7}$]nonane (1.0 g.) in ethanol (50 ml.) was added 5% w/w rhodium on alumina (0.3 g.). The mixture was hydrogenated in an autoclave at 60°–65° C. for 24 hours under 50 atmospheres pressure of hydrogen. Filtration of the product followed by careful evaporation of the solvent gave endo-8-(aminoethyl)tetracyclo[4,3,0,0$^{2,4}$,0$^{3,7}$]nonane as a pale yellow oil. The hydrochloride, m.p. 265.5°–266.5° C. on recyrstallisation from isopropanol, was prepared by addition of ethereal HCl to an ether solution of the free base.

The endo-8-(1-oximinoethyl)tetracyclo[4,3,0,0$^{2,4}$,0$^{3,7}$]nonane used as starting material may be prepared as follows:

The preparation of exo-8-(1-oximinoethyl)tetracyclo[4,3,0,0$^{2,4}$,0$^{3,7}$]nonane as described in Example 6 left reaction liquors which contained both exo- and endo-oxime isomers. Evaporation of ethanol in vacuo from the solution precipitated the mixed isomers as a sticky solid. Samples of this material (2.0 g. each) were submitted to dry column chromatography on 1.0 kg. silica gel (Kieselgel 60, 0.063–0.2 mm. particle size) using as developing solvent a mixture of toluene and ethyl acetate in the ratio of 9:1 v/v. The position of the separated materials on the column was determined by sampling followed by thin-layer chromatography. The regions of the column containing pure exo- and pure endo-isomers were excised and eluted separately with ethyl acetate. Evaporation of the eluates gave an overall yield of pure isomers of approximately 1.2 g. but the actual proportion of exo varied from 0.8–0.2 g. and endo 0.4–1.0 g. depending on the isomer ratio of the sample applied to the column.

Separated by the above method the exo-isomer had m.p. 103°–104° C. and the endo-isomer 80°–83° C.

EXAMPLE 13

Exo-8-(1-aminoethyl)tetracyclo[4,3,0,0$^{2,4}$,0$^{3,7}$]nonane hydrochloride as obtained in Example 6 is a mixture of two diasteroisomers each of which in turn is a mixture of two optical isomers. The same is true of the endo-isomer of Example 12. These diasteroisomers are identifiable as separate spots on thin layer chromatography on silica gel plates using either of two solvent systems. The spots can be visualised in solvent system (1) with either iodine vapour or a ceric ammonium nitrate/sulphuric acid spray followed by heating, or in system (2) by a 1% w/v ninhydrin in butanol spray.

System (1) Toluene/ethanol/ethyl acetate/ammonia (s.g. 0.880) 6:4:2:0.25 v/v/v/v.

System (2) Acetone/ammonia (s.g. 0.880) 40:0.5 v/v

| $R_f$ values | System (1) | System (2) |
|---|---|---|
| Upper exo spot | 0.48 | 0.60 |
| Lower exo spot | 0.43 | 0.54 |
| Upper endo spot | 0.48 | 0.51 |
| Lower endo spot | 0.40 | 0.40 |

The 4 diastereomers can also be identified by the $^{13}$C n.m.r. resonances from the chiral carbon atom of the side chain, while a measure of the relative proportions of each can be gained from the peak height. The actual chemical shift values of each diastereomer varies somewhat with concentration and type of salt, but the mixture of base hydrochlorides obtained in Example 4 gave the following values:

| | Chemical shift from tetramethylsilane in p.p.m. |
|---|---|
| Upper exo spot | 51.9 |
| Lower exo spot | 52.80 |
| Upper endo spot | 52.82 |
| Lower endo spot | 53.6 |

Separation of the exo diastereomers was achieved as follows:

To a solution of exo-8-(1-aminoethyl)tetracyclo[4,3,0,0,$^{2,4}$,0$^{3,7}$]nonane (32.2 g.) in dry ether (250 ml.) was added a solution of L-(+)-tartaric acid (7.16 g., 0.25 mole) in a mixture of ethanol (100 ml.) and dry ether (300 ml.). The precipitate of tartrate salt was filtered off, washed with dry ether and submitted to five fractional crystallisations from ethanol. The final product was pure upper exo spot tartrate (9.0 g.) which was converted via the base to hydrochloride (4.3 g.) which had m.p. 257°–259° C.

Although this method of separation could be expected to effect separation of one of the optically active isomers of a diastereomer, the above product showed zero rotation when examined in a polarimeter and was shown by n.m.r. using an optical shift reagent to be a mixture of equal proportions of the optical isomers.

Addition of a further portion of L-(+)-tartaric acid (7.15 g., 0.25 mole) to the liquors from the first precipitation above gave a sticky precipitate which after two fractional crystallisations from ethanol, followed by conversion to hydrochloride, gave pure lower exo spot material. Recrystallisation of this hydrochloride from ethanol gave a very small first crop (0.12 g.) and a residue of 1.74 g. This first crop proved to be optically active, $[\alpha_D] = +22°$ and by n.m.r. with an optical shift reagent appeared to be a pure optical isomer.

Separation of the lower exo spot on a larger scale was achieved by recovering amine as base from all the fractional crystallisation liquors above (total 13.3 g.), dissolving in dry ether (100 ml.) and adding a solution of D-(−)-mandelic acid (6.2 g., 0.25 mole) in a mixture of ethanol (10 ml.) and dry ether (50 ml.). The precipitated salt (14.6 g.) was fractionally crystallised twice from ethyl acetate, converted to hydrochloride and recrystallised finally from ethanol, to give pure lower exo spot hydrochloride (3.0 g.) m.p. 266°–268° C. This product had zero rotation and was by n.m.r. using an optical shift reagent an equal mixture of the two optical isomers.

A similar process of separation was applied to the endo-amine base (10.8 g.) obtained in Example 12. The L-(+)-tartrate salt was fractionally crystallised five times from isopropanol to give pure upper endo spot tartrate monohydrate (1.16 g.), m.p. 195°–205° C. Residues were converted back to base. The D-(−)-mandelate salt was prepared in ether containing a little alcohol. Three crops were obtained. Crop 1 was fractionally crystallised 3 times from ethyl acetate to give pure upper endo spot mandelate m.p. 191°–192° C. (0.38 g.), while crops 2 and 3 were combined and recrystallised 4 times from ethyl acetate to give pure lower endo spot mandelate (1.1 g.), m.p. 166°–167° C.

EXAMPLE 14

A solution of exo-8-(1-oximinoethyl)tetracyclo[4,3,0,0$^{2,4}$,0$^{3,7}$]nonane (4.0 g.), as obtained in the last section of Example 6, in a mixture of pyridine (35 ml.) and acetic anhydride (30 ml.) was heated under reflux for 48 hours. The solvents were removed in vacuo and the black residue shaken with ether (3×50 ml. portions). Filtration removed black solid and the filtrate was extracted with aqueous 10% w/v sodium bicarbonate solution (3×20 ml.). The organic phase was dried and evaporated giving a brown oil (4.3 g.) which was then chromatographed on silica gel using toluene/ether 9:1 v/v as eluant. The fractions containing single spot material of $R_f$ 0.36 on silica gel t.l.c. plates developed with toluene/ethyl acetate 9:1 v/v were combined and evaporated giving a gum which was crystallised from petroleum ether (b.p. 40°–60° C.). There was obtained a buff solid (0.618 g.) which was then sublimed to give the E-isomer of 8-[1-(diacetylamino)ethylidene]tetracyclo[4,3,0,0$^{2,4}$,0$^{3,7}$]nonane (0.60 g.) (configuration assigned by n.m.r.). Evaporation of the petroleum ether liquors from the crystallisation gave a colourless oil which was distilled in vacuo to give the Z-isomer of 8-[1-(diacetylamino)ethylidene]tetracyclo[4,3,0,0$^{2,4}$,0$^{3,7}$]nonane, b.p. 65°–75°/0.05 mm. (configuration assigned by n.m.r.) (The Z and E nomenclature for double bond isomerism is described in J.Org.Chem., 1970, 35, 2849.)

The E-isomer (377 mg.) was hydrogenated in the presence of platinum oxide (100 mg.) in ethanol (15 ml.) at room temperature and pressure. When the theoretical amount of hydrogen had been absorbed the reaction was filtered and the solvent evaporated leaving a colourless gum. Extraction of this with boiling petroleum ether (b.p. 60°–80° C.) followed by cooling of the extracts gave an amorphous white solid, m.p. 112°–128° C., identified as 8-[1-(acetylamino)ethyl]tetracyclo[4,3,0,0$^{2,4}$,0$^{3,7}$]nonane.

This product was submitted to hydrolysis with concentrated alcoholic caustic potash at reflux for 36 hours. Evaporation of the ethanol, dilution with water and extraction with ether, followed by drying and precipitation with ethereal hydrogen chloride gave 8-(1-aminoethyl)tetracyclo[4,3,0,0$^{2,4}$,0$^{3,7}$]nonane hydrochloride. This product was identified by thin layer chromatography as a mixture of the lower exo spot diastereoisomer and lower endo spot diastereoisomer.

The fact that this product was prepared by cis hydrogenation of a double bond of known stereochemistry permits assignment of the absolute configuration of these two diastereoisomers. This in turn permits assignment of the absolute configuration of the upper exo spot and upper endo spot diastereoisomers. These assignments are as follows:

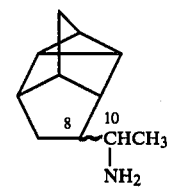

| Diastereoisomer | Absolute configuration |
|---|---|
| Upper exo spot | 8S,10S and 8R,10R |
| Lower exo spot | 8S,10R and 8R,10S |
| Upper endo spot | 8R,10R and 8S,10S |
| Lower endo spot | 8R,10S and 8S,10R |

EXAMPLE 15

To a solution of 8-aminomethyltetracyclo[4,3,0,0$^{2,4}$,0$^{3,7}$]nonane (3.0 g.) prepared by the method of H. K. Hall, J.Org.Chem., 1960, 25, 42, in acetonitrile (60 ml.) was added 37% w/v aqueous formaldehyde solution (7.5 ml.). Sodium cyanoborohydride (2.0 g.) was added in small portions at intervals with stirring so that the temperature did not exceed 35° C. Stirring was continued for a further 20 minutes and then glacial acetic acid was added in sufficient amount to bring the pH to 7. This pH was maintained for 1 hour by occasional addition of acetic acid. The solvents were evaporated in vacuo and the residue partitioned between ether and 2 N NaOH. The ether extracts were dried over anhydrous K$_2$CO$_3$, filtered and treated with excess ethereal hydrogen chloride. The precipitated 8-(dimethylaminomethyl)tetracyclo[4,3,0,0$^{2,4}$,0$^{3,7}$]nonane hydrochloride was recrystallised from isopropanol/ether and had m.p. 245°–246° C. (decomp.).

I claim:

1. A tetracyclononane derivative of the formula:

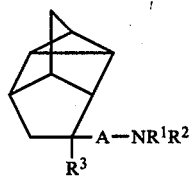

wherein R$^1$ and R$^2$ are hydrogen, R$^3$ is hydrogen or methyl and A is a radical of the formula CH$_2$CH$_2$ or CH—R$^4$ in which R$^4$ is methyl or phenyl or a pharmaceutically-acceptable acid-addition salt thereof.

2. A tetracyclononane derivative as claimed in claim 1 in which A is a radical of the formula CH—$R^4$ in which $R^4$ is methyl.

3. The two diastereoisomers exo-8-(1-aminoethyl)tetracyclo[4,3,0,0$^{2,4}$,0$^{3,7}$]nonane and the pharmaceutically-acceptable acid-addition salts thereof.

4. A pharmaceutical composition comprising a pharmaceutically effective amount of a tetracyclononane derivative of the formula:

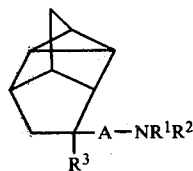

wherein $R^1$ and $R^2$ are hydrogen, $R^3$ is hydrogen or methyl and A is a radical of the formula $CH_2CH_2$ or CH—$R^4$ in which $R^4$ is methyl or phenyl or a pharmaceutically-acceptable acid-addition salt thereof, together with a pharmaceutically-acceptable diluent or carrier.

* * * * *